(12) United States Patent
Littlefield et al.

(10) Patent No.: US 6,653,341 B1
(45) Date of Patent: Nov. 25, 2003

(54) METHODS AND COMPOSITIONS FOR USE IN TREATING CANCER

(75) Inventors: Bruce A. Littlefield, Andover, MA (US); Murray J. Towle, Auburn, NH (US)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/272,167

(22) Filed: Oct. 16, 2002

Related U.S. Application Data

(63) Continuation-in-part of application No. 09/843,617, filed on Apr. 26, 2001, now Pat. No. 6,469,182, which is a continuation of application No. 09/677,485, filed on Oct. 2, 2000, now Pat. No. 6,365,759, which is a continuation of application No. 09/334,488, filed on Jun. 16, 1999, now Pat. No. 6,214,865.
(60) Provisional application No. 60/089,682, filed on Jun. 17, 1998.

(51) Int. Cl.[7] ............................................. A61K 31/35
(52) U.S. Cl. ....................................................... 514/450
(58) Field of Search ........................................... 514/450

(56) References Cited

U.S. PATENT DOCUMENTS

| 5,338,865 A | 8/1994 | Kishi et al. ................. 549/214 |
| 5,436,238 A | 7/1995 | Kishi et al. ................. 549/214 |
| 6,214,865 B1 | 4/2001 | Littlefield et al. ........... 514/450 |
| 6,365,759 B1 | 4/2002 | Littlefield et al. ........... 549/414 |
| 6,469,182 B1 | 10/2002 | Littlefield et al. .......... 549/214 |

FOREIGN PATENT DOCUMENTS

| EP | 0 572 109 A1 | 12/1993 |
| WO | WO 93/17690 | 9/1993 |

OTHER PUBLICATIONS

Aicher et al., "Total Synthesis of Halichondrin B and Norhalichondron B," J. Am. Chem. Soc. 114:3162–3164 (1992).

Horita et al., "Synthetic Studies of Halichondrin B, an Antitumor Polyether Macrolide Isolated from a Marine Sponge. 8. Synthesis of the Lactone Part (C1–C36) via Horner–Emmons Coupling Between C1–C15 and C16–C36 Fragments and Yamaguchi Lactonization," Tetrahedron Letters 38:8965–8968 (1997).

Stamos et al., "New Synthetic Route to the C.14–C.38 Segment of Halichondrins," J. Org. Chem. 62:7552–7553 (1997).

*Primary Examiner*—Amelia A. Owens
(74) *Attorney, Agent, or Firm*—Clark & Elbing LLP

(57) ABSTRACT

The invention provides methods and compositions for use in treating diseases associated with excessive cellular proliferation, such as cancer.

33 Claims, No Drawings

METHODS AND COMPOSITIONS FOR USE IN TREATING CANCER

CROSS REFERENCE TO RELATED APPLICATIONS

This application is a continuation-in-part of claims priority from U.S. Patent application Ser. No. 09/843,617, filed Apr. 26, 2001which is a continuation of U.S. Patent application Ser. No. 09/677,485, filed Oct. 2, 2000 (now U.S. Pat. No. 6,365,759), which is a continuation of U.S. Patent application Ser. No. 09/334,488, filed Jun. 16, 1999 (now U.S. Pat. No. 6,214,865), which claims priority from U.S. Provisional Patent Application Ser. No. 60/089,682, filed Jun. 17, 1998 (now abandoned). The contents of the earlier filed applications are incorporated by reference herein in their entirety.

FIELD OF THE INVENTION

This invention relates to methods and compositions for use in treating cancer.

BACKGROUND OF THE INVENTION

Cancer is a term used to describe a wide variety of diseases that are each characterized by the uncontrolled growth of a particular type of cell. It begins in a tissue containing such a cell and, if the cancer has not spread to any additional tissues at the time of diagnosis, may be treated by, for example, surgery, radiation, or another type of localized therapy. However, when there is evidence that cancer has metastasized from its tissue of origin, different approaches to treatment are typically used. Indeed, because it is not possible to determine the extent of metastasis, systemic approaches to therapy are usually undertaken when any evidence of spread is detected. These approaches involve the administration of chemotherapeutic drugs that interfere with the growth of rapidly dividing cells, such as cancer cells.

Halichondrin B is a structurally complex, macrocyclic compound that was originally isolated from the marine sponge *Halichondria okadai*, and subsequently was found in Axinella sp., *Phakellia carteri*, and Lissondendryx sp. A total synthesis of halichondrin B was published in 1992 (Aicher et al., J. Am. Chem. Soc. 114:3162-3164, 1992). Halichondrin B has been shown to inhibit tubulin polymerization, microtubule assembly, beta$^s$-tubulin crosslinking, GTP and vinblastine binding to tubulin, and tubulin-dependent GTP hydrolysis in vitro. This molecule has also been shown to have anti-cancer properties in vitro and in vivo. Halichondrin B analogs having anti-cancer activities are described in U.S. Pat. No. 6,214,865 B1.

SUMMARY OF THE INVENTION

The invention provides methods of treating cancer in a patient, involving administration of a compound having the formula:

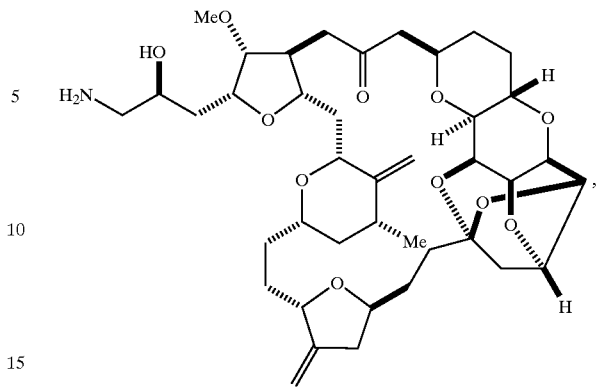

or a pharmaceutically acceptable salt thereof, which is carried out in combination with a second approach to treatment.

The second approach to treatment can involve administration of a chemotherapeutic drug to the patient. Examples of types of such drugs include antimetabolites, antibiotics, alkylating agents, plant alkaloids, and hormonal agents.

An antimetabolite, such as gemcitabine, can be used in the invention in the treatment of, for example, non-small cell lung carcinoma, pancreatic cancer, or metastatic breast cancer. An antimetabolite, such as capecitabine, can also be used in the invention in the treatment of, for example, breast cancer or colorectal cancer.

An example of a type of antibiotic that can be used in the invention is anthracyclines (e.g., doxorubicin), which can be used in the invention, for example, in the treatment of breast cancer.

Alkylating agents, such as, for example, carboplatinum or cisplatinum, can be used in the invention to treat, for example, non-small cell lung cancer or ovarian cancer.

Plant alkaloids, such as irinotecan and topotecan, can be used in the invention to treat, for example, colorectal cancer, ovarian cancer, or non-small cell lung carcinoma.

The second approach to treatment can also involve administration of an anticoagulant or antithrombotic agent (e.g., heparin) to the patient.

The invention also provides compositions that include a compound having the formula:

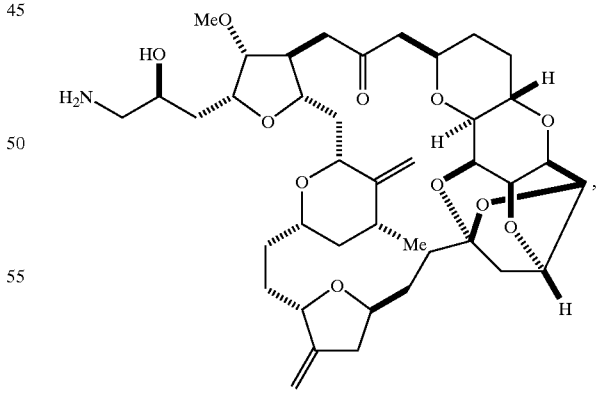

or a pharmaceutically acceptable salt thereof, in combination with a second anti-cancer drug. These drugs include, for example, any of the chemotherapeutic agents mentioned elsewhere herein, as well as others.

Other features and advantages of the invention will be apparent from the following detailed description and the claims.

DETAILED DESCRIPTION OF THE INVENTION

The invention provides methods for treating cancer, involving administration of a halichondrin B analog, such as an analog having the following structure:

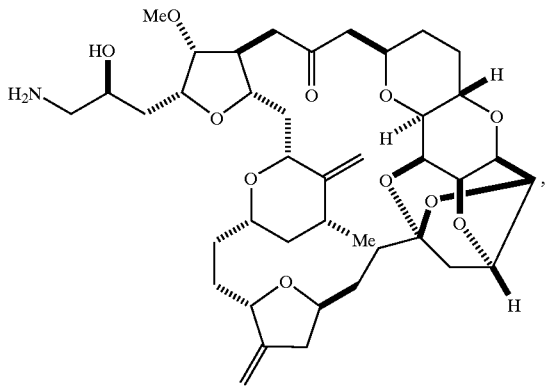

which is carried out in combination with a second approach to treatment.

There are numerous types of anti-cancer approaches that can be used in conjunction with halichondrin B analog treatment, according to the invention. These include, for example, treatment with chemotherapeutic agents (see below), biological agents (e.g., hormonal agents, cytokines (e.g., interleukins, interferons, granulocyte colony stimulating factor (G-CSF), macrophage colony stimulating factor (M-CSF), and granulocyte macrophage colony stimulating factor (GM-CSF)), chemokines, vaccine antigens, and antibodies), anti-angiogenic agents (e.g., angiostatin and endostatin), radiation, and surgery.

The methods of the invention can employ these approaches to treat the same types of cancers as those for which they are known in the art to be used, as well as others, as can be determined by those of skill in this art. Also, these approaches can be carried out according to parameters (e.g., regimens and doses) that are similar to those that are known in the art for their use. However, as is understood in the art, it may be desirable to adjust some of these parameters, due to the additional use of a halichondrin B analog with these approaches. For example, if a drug is normally administered as a sole therapeutic agent, when combined with a halichondrin B analog, according to the invention, it may be desirable to decrease the dosage of the drug, as can be determined by those of skill in this art. Examples of the methods of the invention, as well as compositions that can be used in these methods, are provided below.

Chemotherapeutic drugs of several different types including, for example, antimetabolites, antibiotics, alkylating agents, plant alkaloids, hormonal agents, anticoagulants, antithrombotics, and other natural products, among others, can be used in conjunction with halichondrin B treatment, according to the invention. Specific, non-limiting examples of these classes of drugs, as well as cancers that can be treated by their use, are as follows.

Antimetabolite drugs that halichondrin B analogs can be used with include, e.g., methotrexate, purine antagonists (e.g., mercaptopurine, thioguanine, fludarabine phosphate, cladribine, and pentostatin), and pyrimidine antagonists (e.g., gemcitabine, capecitabine, fluorouracil (e.g., 5-FU), cytarabine, and azacitidine). Use of these agents to treat particular types of cancers is well known in the art, and these agents can be used in combination with halichondrin B analogs to treat these and other types of cancers. As specific, non-limiting examples, a halichondrin B analog can be used with gemcitabine in the treatment of non-small cell lung carcinoma, pancreatic cancer, or metastatic breast cancer. In an additional example, a halichondrin B analog can be used in conjunction with capecitabine in the treatment of breast or colorectal cancers.

As is noted above, another class of chemotherapeutic drugs with which halichondrin B analogs can be used includes anticancer antibiotics. These include, for example, anthracyclines (e.g., doxorubicin, epirubicin, daunorubicin, and idarubicin), adriamycin, dactinomycin, idarubincin, plicamycin, mitomycin, and bleomycin. As with the drugs mentioned above, use of these agents to treat particular types of cancers is well known in the art, and they can be used in combination with halichondrin B analog treatment to treat these and other types of cancers. As a specific, non-limiting example, an anthracycline, such as doxorubicin, can be administered in conjunction with halichondrin B therapy for the treatment of breast or pancreatic cancers. Alternatively, a third agent, cyclophosphamide, can be used in this method.

Alkylating agents comprise another class of chemotherapeutic drugs that can be administered in conjunction with a halichondrin B analog, according to the invention. Examples of such drugs include procarbazine, dacarbazine, altretamine, cisplatin, carboplatin, and nitrosoureas. Halichondrin B analogs can be used with these agents in the treatment of cancers that these agents are known in the art to be used to treat, as well as in the treatment of other cancers. For example, a halichondrin B analog can be used in conjunction with carboplatinum in the treatment of non-small cell lung carcinoma or ovarian cancer.

An additional type of chemotherapeutic drug with which halichondrin B analogs can be administered, according to the invention, is plant alkaloids, such as vinblastine, vincristine, etoposide, teniposide, topotecan, irinotecan, paclitaxel, and docetaxel. As specific, non-limiting examples, a halichondrin B analog can be used in conjunction with irinotecan for the treatment of colorectal cancer, or with topotecan in the treatment of ovarian or non-small cell lung cancers.

Further types of anti-cancer agents that can be used in conjunction with halichondrin B analog treatment, according to the invention, are anticoagulants and antithrombotic agents. For example, heparin (e.g., low molecular weight heparin or heparin sulfate) or warfarin can be used. Use of these agents in treating patients by, for example, injection or oral administration, is well known in the art, and thus they can readily be adapted by those of skill in the art for use in the present invention.

Numerous approaches for administering anti-cancer drugs are known in the art, and can readily be adapted for use in the present invention. In the case of one or more drugs that are to be administered in conjunction with a halichondrin B analog, for example, the drugs can be administered together, in a single composition, or separately, as part of a comprehensive treatment regimen. For systemic administration, the drugs can be administered by, for example, intravenous infusion (continuous or bolus). Appropriate scheduling and dosing of such administration can readily be determined by those of skill in this art based on, for example, preclinical studies in animals and clinical studies (e.g., phase I studies) in humans. In addition, analysis of treatment using similar drugs, as well as monitoring factors such as blood counts (e.g., neutrophil and platelet counts) and vital signs in patients can be used, as is well understood in the art.

Many regimens used to administer chemotherapeutic drugs involve, for example, intravenous administration of a drug (or drugs) followed by repetition of this treatment after a period (e.g., 1–4 weeks) during which the patient recovers from any adverse side effects of the treatment. It may be desirable to use both drugs at each administration or, alternatively, to have some (or all) of the treatments include only one drug (or a subset of drugs).

As a specific, non-limiting example of a treatment regimen included in the invention, a halichondrin B analog (e.g., 0.01–5 mg/m$^2$) can be administered to a patient by intravenous infusion for 0.5–3 hours, followed by intravenous infusion of another drug (e.g., gemcitabine, e.g., 500–900 mg/m$^2$) for 0.5–3 hours. This course of treatment can be repeated every 2–3 weeks, as determined to be tolerable and effective by those of skill in the art. In a variation of this method, the treatment is carried out with both drugs on the first day, as is noted above, but then is followed up with treatment using only the secondary drug (e.g., gemcitabine) in ensuing weeks.

Further, as is well known in the art, treatment using the methods of the invention can be carried out in conjunction with the administration of antiemetics, which are drugs that are used to reduce the nausea and vomiting that are common side effects of cancer chemotherapy. Examples of such drugs include major tranquilizers (e.g., phenothiazines, such as chlorpromazine and prochlorperazine), dopamine antagonists (e.g., metoclopramide), serotonin antagonists (e.g., ondansetron and granisetron), cannabinoids (e.g., dronabinol), and benzodiazepine sedatives.

In addition to the cancers mentioned above, the methods and compositions of the invention can be used to treat the following types of cancers, as well as others: skin (e.g., squamous cell carcinoma, basal cell carcinoma, or melanoma), prostate, brain and nervous system, head and neck, testicular, lung, liver (e.g., hepatoma), kidney, bladder, gastrointestinal, bone, endocrine system (e.g., thyroid and pituitary tumors), and lymphatic system (e.g., Hodgkin's and non-Hodgkin's lymphomas) cancers. Other types of cancers that can be treated using the methods of the invention include fibrosarcoma, neurectodermal tumor, mesothelioma, epidermoid carcinoma, and Kaposi's sarcoma.

The invention also includes compositions that include a halichondrin B analog in combination with an additional therapeutic agent(s), such as any of those agents listed above. The drugs in these compositions preferably are formulated for administration to patients (e.g., in physiological saline) or, alternatively, can be in a form requiring further processing prior to administration. For example, the compositions can include the drugs in a lyophilized form or in a concentrated form requiring dilution. Formulation of drugs for use in chemotherapeutic methods can be carried out using standard methods in the art (see, e.g., *Remington's Pharmaceutical Sciences* (81$^{th}$ edition), ed. A. Gennaro, 1990, Mack Publishing Co., Easton, Pa.).

What is claimed is:

1. A method of treating cancer in a patient, said method comprising administering to said patient a compound having the formula:

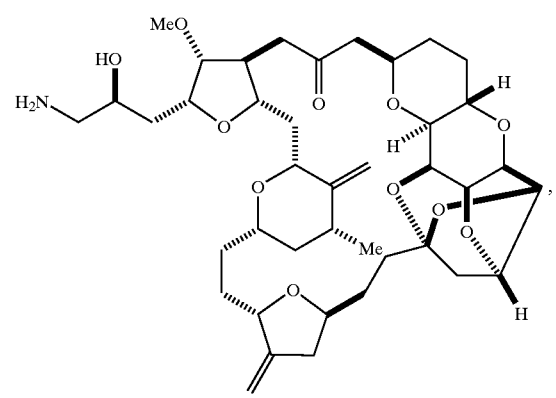

or a pharmaceutically acceptable salt thereof, in combination with a second approach to treatment.

2. The method of claim 1, wherein said second approach to treatment comprises administration of a chemotherapeutic drug to said patient.

3. The method of claim 2, wherein said chemotherapeutic drug is selected from the group consisting of antimetabolites, antibiotics, alkylating agents, plant alkaloids, and hormonal agents.

4. The method of claim 3, wherein said chemotherapeutic drug is an antimetabolite.

5. The method of claim 4, wherein said antimetabolite is gemcitabine.

6. The method of claim 5, wherein said cancer is non-small cell lung carcinoma, pancreatic cancer, or metastatic breast cancer.

7. The method of claim 4, wherein said antimetabolite is capecitabine.

8. The method of claim 7, wherein said cancer is breast cancer or colorectal cancer.

9. The method of claim 3, wherein said antibiotic is an anthracycline.

10. The method of claim 9, wherein said anthracycline is doxorubicin.

11. The method of claim 10, wherein said cancer is breast cancer.

12. The method of claim 3, wherein said chemotherapeutic drug is an alkylating agent.

13. The method of claim 12, wherein said alkylating agent is carboplatinum or cisplatinum.

14. The method of claim 13, wherein said cancer is non-small cell lung cancer or ovarian cancer.

15. The method of claim 3, wherein said chemotherapeutic drug is a plant alkaloid.

16. The method of claim 15, wherein said plant alkaloid is irinotecan.

17. The method of claim 16, wherein said cancer is colorectal cancer.

18. The method of claim 15, wherein said plant alkaloid is topotecan.

19. The method of claim 18, wherein said cancer is ovarian cancer or non-small cell lung cancer.

20. The method of claim 1, wherein said second approach to treatment comprises administration of an anticoagulant to said patient.

21. The method of claim 20, wherein said anticoagulant is heparin.

22. A composition comprising a compound having the formula:

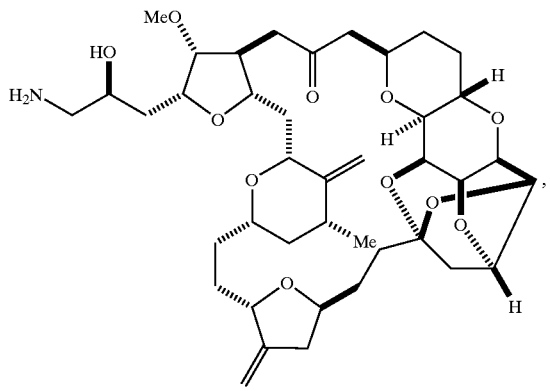

or a pharmaceutically acceptable salt thereof, in combination with a second chemotherapeutic drug.

23. The composition of claim 22, wherein said chemotherapeutic drug is selected from the group consisting of antimetabolites, antibiotics, alkylating agents, plant alkaloids, and hormonal agents.

24. The composition of claim 23, wherein said chemotherapeutic drug is an antimetabolite.

25. The composition of claim 24, wherein said antimetabolite is gemcitabine.

26. The composition of claim 24, wherein said antimetabolite is capecitabine.

27. The composition of claim 23, wherein said antibiotic is an anthracycline.

28. The composition of claim 27, wherein said anthracycline is doxorubicin.

29. The composition of claim 23, wherein said chemotherapeutic drug is an alkylating agent.

30. The composition of claim 29, wherein said alkylating agent is carboplatinum or cisplatinum.

31. The composition of claim 23, wherein said chemotherapeutic drug is a plant alkaloid.

32. The composition of claim 31, wherein said plant alkaloid is irinotecan.

33. The composition of claim 31, wherein said plant alkaloid is topotecan.

* * * * *